US005747459A

United States Patent [19]
Rowe et al.

[11] Patent Number: 5,747,459
[45] Date of Patent: May 5, 1998

[54] METHOD FOR INSURING ADEQUATE INTRACELLULAR GLUTATHIONE IN TISSUE

[75] Inventors: W. Bruce Rowe, Evanston; David A. Mark, Oak Park; David C. Madsen, Libertyville, all of Ill.

[73] Assignee: Nestec, Ltd., Vevey, Switzerland

[21] Appl. No.: 795,150

[22] Filed: Feb. 7, 1997

Related U.S. Application Data

[63] Continuation of Ser. No. 659,111, Jun. 3, 1996, abandoned, which is a continuation of Ser. No. 306,133, Sep. 14, 1994, abandoned, which is a continuation-in-part of Ser. No. 650,222, Feb. 4, 1991, abandoned.

[51] Int. Cl.$^6$ .............................. A23J 1/20; A23C 23/00; A23C 35/00
[52] U.S. Cl. ............................................. 514/18; 530/331
[58] Field of Search ............................... 514/18; 530/331

[56] References Cited

U.S. PATENT DOCUMENTS

| | | | |
|---|---|---|---|
| 2,712,202 | 7/1955 | Hosler et al. | 424/246 |
| 3,737,536 | 6/1973 | Sagner et al. | 424/246 |
| 3,755,578 | 8/1973 | McFarland et al. | 424/246 |
| 4,001,437 | 1/1977 | Jaeggi et al. | 426/34 |
| 4,016,293 | 4/1977 | Coughlin | 514/2 |
| 4,175,130 | 11/1979 | Yamanaka et al. | 514/369 |
| 4,335,210 | 6/1982 | Meister et al. | 378/112 |
| 4,338,315 | 7/1982 | Paget et al. | 514/227.2 |
| 4,398,026 | 8/1983 | Takano et al. | 514/227.2 |
| 4,420,479 | 12/1983 | Morwick et al. | 514/227.2 |
| 4,427,658 | 1/1984 | Maubois et al. | 426/7 |
| 4,434,158 | 2/1984 | Meister et al. | 424/94.63 |
| 4,438,124 | 3/1984 | Meister et al. | 514/369 |
| 4,482,574 | 11/1984 | Lee | 426/7 |
| 4,563,471 | 1/1986 | Satzinger et al. | 514/369 |
| 4,636,388 | 1/1987 | Lin et al. | 426/7 |
| 4,647,453 | 3/1987 | Meisner | 424/54 |
| 4,647,571 | 3/1987 | Meister et al. | 514/369 |
| 4,665,082 | 5/1987 | Meister et al. | 514/365 |
| 4,710,489 | 12/1987 | Meister | 514/18 |
| 4,752,618 | 6/1988 | Mascioli et al. | 514/549 |
| 4,775,675 | 10/1988 | Gyorgydeak et al. | 514/307 |
| 4,780,475 | 10/1988 | Cerra et al. | 514/561 |
| 4,784,685 | 11/1988 | Meister | 514/18 |
| 4,791,125 | 12/1988 | Clark | 514/369 |
| 4,798,835 | 1/1989 | Krupp et al. | 514/369 |
| 4,839,387 | 6/1989 | Poli | 514/19 |
| 4,868,114 | 9/1989 | Nagasawa et al. | 435/112 |
| 4,963,577 | 10/1990 | Schorlemmer et al. | 514/369 |
| 4,981,704 | 1/1991 | Thibault | 426/41 |
| 5,002,953 | 3/1991 | Hindley | 514/275 |
| 5,028,627 | 7/1991 | Kilbourn et al. | 435/68.1 |
| 5,039,609 | 8/1991 | Klein | 514/275 |
| 5,053,387 | 10/1991 | Alexander | 271/280 |
| 5,055,446 | 10/1991 | Alexander et al. | 424/450 |
| 5,089,268 | 2/1992 | Katz | 424/450 |
| 5,095,027 | 3/1992 | Goldberg et al. | 514/369 |
| 5,158,883 | 10/1992 | Griffith | 435/240.2 |
| 5,208,249 | 5/1993 | Rowe et al. | 65/172 |

FOREIGN PATENT DOCUMENTS

| | | |
|---|---|---|
| 0 002 978 | 12/1978 | European Pat. Off. . |
| 0 257 992 | 6/1987 | European Pat. Off. . |
| 0 318 330 | 11/1988 | European Pat. Off. . |
| 0 327 263 | 1/1989 | European Pat. Off. . |
| 0 338 459 | 4/1989 | European Pat. Off. . |
| 0 373 002 | 12/1989 | European Pat. Off. . |
| 0 374 390 | 6/1990 | European Pat. Off. . |
| 0 415 598 | 8/1990 | European Pat. Off. . |
| 2 141 765 | 3/1973 | Germany . |
| 47 8537 | 3/1972 | Japan . |
| 84/03625 | 9/1984 | WIPO . |
| 91/14424 | 3/1991 | WIPO . |
| 93/11104 | 10/1993 | WIPO . |

OTHER PUBLICATIONS

Clintec Nutrition Company, Peptamen® Brochure (1987).
Clintec Nutrition Company, Peptamen® Brochure (1990).
Clintec Nutrition Company, *Carnation® Peptamen® Liquid, Isotonic, Complete, Elemental Diet: Clinical Rationale* (1987).
Clintec Nutrition Company, *Evaluation of a Peptide–Based Elemental Diet versus an Amino Acid Based Elemental Diet in Geriatric Tube–Fed Patients* (1987).
Clintec Nutrition Company, *Carnation® Liquid Elemental Diet Flavoring Ideas* (1988).
Clintec Nutrition Company, *Use of PEPTAMEN™ Liquid, Isotonic, Complete, Elemental Diet in The Transition from TPN and Long–Term Management on Enteral Feeding* (1987).
Clintec Nutrition Company, *Use of PEPTAMEN™ Liquid, Isotonic, Complete, Elemental Diet in a Patient with a High–Output Ostomy* (1987).
Clintec Nutrition Company, *The Case for Peptides in a Defined Formula* (1988).
Clintec Nutrition Company, *The Case for a Balance–Energy–Substrate Formula* (1988).
Feller et al, "Effects of Three Liquid Diets on Nutrition–Sensitive Plasma Proteins of Tube–Fed Elderly Men," *J. of Am. Geriatrics Soc'y*, No. 6, pp. 663–668 (1990).
Polk et al, "Intermittent Administration of a Defined Formula Diet Induces Growth in Adolescents With Crohn's Disease and Growth Failure," *Pediatric Res.* Abstract No. 664, 113A (1990).
Mandel, et al. *Intracellular Glutathione in the Protection from Anoxic injury in Renal Proximal Tubles*, J. Clin. Invest., 1990, vol. 85, No. 2, pp. 316–324. (Abstract).

(List continued on next page.)

Primary Examiner—Cecilia J. Tsang
Assistant Examiner—Lynn Touzeau
Attorney, Agent, or Firm—Hill, Steadman & Simpson

[57] ABSTRACT

A method is provided for increasing and/or maintaining the level of intracellular glutathione. Pursuant to the invention, compositions including denatured and at least partially hydrolyzed proteins are administered to a patient in an amount sufficient to increase glutathione levels in the patient.

20 Claims, 7 Drawing Sheets

OTHER PUBLICATIONS

Chang, et al., *Cytoprotective Effect of Reduced Glutathione in Arsenical–Iduced Endothelial Cell injury*, Toxicology, 1991, vol. 69, No. 1, pp. 101–110. (Abstract).

Moslen, *Protection by L–2–Oxothiazolidine–4–Carboxylate, a Cysteine Prodrug, Against 1.1–Dichlorethylene Hepatotoxicity in Rats is Associated with Decreased in Toxin Metabolism and Cytochrome P–450*, J. Pharmacol. Exp. Ther., vol. 248, No. 1, pp. 157–63. (Abstract).

Cretton, et al., *Catabolism of 3'–Axido–3'Deoxythymidine in Hepactocytes and Liver Microsomes, with Evidence of Formation of 3'–Amino–3'–Deoxythmidine, a Highly Toxic Catabolite for Human Bone Marrow Cells*, Molecular Pharmacology, vol. 39, pp. 258–266, 1991.

Handlon, et al. *Thiol Reduction of 3'–Aziodthymidine to 3'–Aminothymidine: Kinetics and Biomedical Implications*, Pharmaceutical Research, vol. 5, No. 5, pp. 297–299, 1988.

Lamperth, et al. *Abnormal Skeletal and Cardiac Muscle Mitochondria Induced by Zidovudine (AZT) in Human Muscle in vitro and in an Animal Model*, Laboratory Investigation, vol. 65, No. 6, pp. 742–752, 1991.

Bone, et al. *Definitions for Sepsis and Organ Failure*, Critical Care Medicine, 1992, vol. 20, No. 6, pp. 724–725.

American College of Chest Physicians/Society of Critical Care Medicine Consensus Conference Committee, *American College of Chest Physicians/Society of Critical Care Medicine Consensus Conference: Definitions for Sepsis and Organ Failure and Guidelines for the Use of Innovative Therapies in Sepsis*, Critical Care Medicine, Jun. 1992, vol. 20, No. 6, pp. 864–874.

Kilbourn et al., *Inhibition of Interleukin–1–α–Induced nitric Oxide Synthase in Vascular Smooth Muscle and Full Reversal of Interleukin–1–α induced Hypotension by $N^{107}$ –Amino–L=Argine*, Journal of the National Cancer Institute, Jul. 1, 1992, vol. 84, No. 13, pp. 1008–1016.

Osol, et al. Eds., *Reminington's Pharmaceutical Sciences*, 1980, Sixteenth Edition.

W. Lucht et al., *Prevention of Release of Granulocyte Aggregants into Sheep Lung Lymph Follownig Endotoxemia by N–Acetylcysteine*, The American Journal of the Medical Sciences, vol. 294, No. 3, Sep. 1987, pp. 161–167.

G. Bernard et al., *Effect of N–Acetylcysteine on the Pulmonary Response to Endotoxin in the Awake Sheep, and Upon In Vitro Granulocyte Function*, J. Clin. Invest., vol. 73, Jun. 1984, pp. 1772–1784.

A. Cantin et al., *Normal Alveolar Epithelial Lining Fluid Contains High Levels of Glutathione*, pp. 152–157.

L. Smith et al. *Effect of Fasting on Hyperoxic Lung Injury in Mice*, Am. Rev. Respir. Dis. 1990; 141:141–149.

J. Strausz et al. *Oxygen Radical Production by Alveolar Inflammatory Cells in Idiopathic Pulmonary Fibrosis*, Am. Rev. Respir. Dis. 1990; 141:124–128.

A. Cantin et al., *Glutathione Deficiency in the Epithelial Lining Fluid of the Lower Respiratory Tract in Idiopathic Pulmonary Fibrosis*, Am. Rev. Respir. Dis. 1989; 139:370–372.

A. Cantin et al., *Oxidants, Antioxidants and the Pathogenesis of Emphysema*, Eur. J. Respi. Dist (1985) 66, Suppl. 139. pp.7–17.

I. Cotgreave et al. *Lung and Systemic Thiol Homeostasis During an Acute Lung Inflammation in the Rat*, Toxicology, 50 (1988), pp. 331–343.

J. Sun et al. *Effects of Buthionine Sulfoximine on the Development of Ozone–Induced Pulmonary Fibrosis*, Experimental and Molecular Pathology 49 (1988), pp. 254–266.

S. Baldwin et al. *Oxidant Activity in Expired Breath of Patients with Adult Respiratory Distress Syndrome*, The Lancet, Jan. 4, 1986, pp. 11–14.

M.F. Tsan et al. *Enhancement of Intracellular Glutathione Protects Endothelial Cells Against Oxidant Damage*, Biochemical and Biophysical Research Communications, vol. 127, No. 1, Feb. 28, 1985, pp. 270–276.

M.F. Tsan et al. *L–2–Oxothiazolidine–4–Carboxylate Protects Endothelial Cells Against Hperopia–Induced Injury*, Inflammation, vol. 12, No. 2, 1988, pp. 113–121.

P.H.S. Sporn et al. *Complex Effects of In Vitro Hyperoxia on Alveolar Macrophage Arachidonic Acid Metabolism*, American Journal of Respiratory Cell and Molecular Biology, vol. 2, No. 1, Jan. 1990, pp. 81–90.

M.A. Passero et al., *L–2–Oxothiazolidine–4–Carboxylic Acid Increases Glutathione in Mouse Lung*, A. Rev. Respir. Dis. vol. 133, 1986, p. A395. (Abstract).

Uhlig, et al. *Glutathione Enhancement in Various Mouse Organs and Protection by Glutathione Isopropyl Ester Against Liver Injury*, Jun. 15, 1990, pp. 1877–1880.

Bellin, et al., *Purification of Glycosaminoglycens from Bovine Follicular Fluid*, J. Dairy Sci., No. 9, 1987, vol. 70, pp. 1913–1919.

Calvin, et al., *Estimation and Manipulation of Glutathione Levels in Prepuberal Mouse Ovaries and Ova: Relevance to Sperm Nucleus Transformation in the Fertilized Egg*, Gamete Research, 1986, vol. 14, pp. 265–275.

Gordon et al., *Applications of Micromanipulation to Human in Vitro Fertilization*, Journal of In Vitro Fertilization and Embryo Transfer, 1988, vol. 5, No. 2, pp. 57–60.

Perreault, et al. *Importance of Glutathione in the Acquisition and Maintenance of Sperm Nuclear Decondensing Activity in Maturing Hamster Oocytes*, Developmental Biology, 1988, vol. 125, pp. 181–186.

Perreault, et al. *The Timing of Hamster Sperm Nuclear Decondensation and Male Pronucleus Formation is Related to Sperm Nuclear Disulfide Bond Content*, Biology of Reproduction, 1987, vol. 36, pp. 239–244.

Perreault, et al. *The Role of Disulfide Bond Reduction During Mammalian Sperm Nuclear Decondensation in Vivo*, Developmental Biology, 1984, vol. 101, pp. 160–167.

Reyes, et al., *Hesparin and Glutathione: Physiological Decondensing Agents of Human Sperm Nuclei*, Gamete Research, 1989, vol. 23, pp. 39–47.

Zirkin, et al., *In Vitro and In Vivo Studies of Mammalian Sperm Nuclear Decondensation*, Gamete Research, 1985, vol. 11, pp. 349–365.

Shapiro, *The Control of Oxidant Stress at Fertilization*, Science, Apr. 26, 1991, pp. 533–536.

Oeriu, et al. *4–Thiazolidinecarboxylic Acids for Live–Stock Raising*, Ger. Offen. Oct. 22, 1970, p. 17. (Abstract).

Slaweta, et al., *The Effect of Glutathione on the Motility and Fertility of Frozen Bull Sperm*, Amin. Reprod. Sci., 1987, vol. 13, No. 4., pp. 249–253. (Abstract).

Lasalle, et al., *Relationship Between Fertilizing Ability of Frozen Human Spermatozoa and Capacity for Heparin Binding and Nuclear Decondensation*, J. Reprod. Fertil, 1992, vol. 95, No. 2, pp. 313–324.(Abstract).

Bounous et al., *The influence of dietary where protein on tissue glutathione and the diseases of aging*, Clinical Invest. Med., vol. 12, No. 6, pp. 343–349, 1989. (Abstract).

Kuzuya, et al., *Protective role of intracellular glutathione against oxidized low density lipoprotein in cultured endothelial cells*, Biochem. Biophys. Res. Commun 163 (3) 1989 (Abstract).

Roseneld et al, *Macrophage–derived Foam Cells Freshly Isolated from Rabbit Athersclerotic Lesions Degrade Modified Lipoproteins. promote Oxidation of Low–Density Lipoproteins, and Contain Oxidation–specific Lip–protein Adducts*, The American Society for Clinical Investigation, Inc., 1991, vol. 87, pp. 90–99.

Heinecke, et al. *The Role of Sulfur–containing Amino Acids in Superoxide Production and odification of Low Density Lipoprotein by Arterial Smooth Muscle Cells*, The Journal of Biologicla Chemistry, 1987, Vool. 262, No. 21, pp. 10098–10103.

Parthasarathy, *Oxidation of low–density lipoprotein by thiol compounds leads to its recognition by the acetyl LDL receptor*, Biochimica et Biophysica Acta, 917, 1987, pp. 337–340.

Kalebic, eta l., *Suppression of human immunodeficiency virus expression in chronically infected moncytic cells by glutathione, glutathione ester, and N–acetycysteine*, Proc. Natl. Acad. Sci. USA, 1991. (Abstract).

Gustafson, et al. *Aids–Antiviral Sulfolipids from Cyanobacteria (Blue–Green Algae)*, J. Natl. Cancer Inst., 1989, vol. 81, No. 16, pp. 1254–1258. (Abstract).

Prendergast et al., *Arachidonic Acid–Binding Peptides, Antibodies Produced to these Peptides and unsaturated Fatty Acid Compounds Having Afinity for the Peptides for Therapy, Pharmaceuticals and Product Sterilization*, Chemical Abstracts, 1992, vol. 116, p. 84, (Abstract).

Frankova, *The Effects of Amino Acids with Sulfhydryl Group on Herpest Viruses in Vitro*, Acla Virol, Engl. Ed. (1967), vol. 11, No. 6, pp. 559–561.

Abate, et al. *Redox Regulation of Fos and jun DNA–Binding Activity in Vitro*, Science, Sep. 1990, vol. 249, pp. 1157–1161.

Duh, et al. *Tumor Necrosis Factor α Activates Human Immunodeficiency Virus Type 1 Through Induction of Nuclear Factor Binding to the NF-$_κ$B Sites in the Long Terminal Repeat*, Proc. Natl. Acad. Sci. USA, Aug. 1989, vol. 86, pp. 5974–5978.

Staal, et al. *Intracellular Thiols Regulate Activation of Nuclear Factor $_κ$B and Transcription of Human Immunodeficiency Virus*, Proc. Natl. Acad. Sci. USA, Dec. 1990, vol. 87, pp. 9943–9947.

Mihm et al. *Inhibition of HIV–1 Replication and NF–$_χ$B activity by Cysteine and Cysteine Derivatives*, Aids 1991, vol. V, No. 5, pp. 497–503.

Stevens, *Human Herpesviruses, a Consideration of the Latent State*, Microbiological Reviews, Sep. 1989, pp. 318–332.

Schnittman,et al., *The Reservoir for HIV–1 in Human Peripheral Blood is a T Cell that Maintains Expression of CD4*, Science, Jul. 21, 1989, vol. 245, pp. 305–308.

Peristeris, et al. *N–Acetylcystein and Glutathione as Inhibitors of Tumor Necrosis Factor Production*, Cell. Immunol., 1992, vol. 140, No. 2, pp. 390–399. (Abstract).

Keller, et al. *Decreased Hepatic Gluthatione Levels in Septic Shock, Predisposition of Hepatocytes to Oxidative Stress: an Experimental Approach*, Arch. Surg. (Chicago), 1985, vol. 120, No. 8, pp. 941–945. (Abstract).

Pacht, et al. *Deficiency of Alveolar Fluid Glutathione in Patients with Sepsis and the Adult Respiratory Distress Syndrome*, Chest, 1991, vol. 100, No. 5, pp. 1397–1403 (Abstract).

Flaherty, et al., *Reperfusion Injury*, Free Radical Biology & Medicine, 1988, Vol. 5, pp. 409–419.

Darley–Usmar, et al. *Oxygen and Reperfusion Damage: an Overview*, Free Radi. Res. Comms., vol. 7, No. 36, pp. 247–254, 1989.

Lachman, et al. *The theory and Practice of Industrial Pharmacy*, 1976, 2d Ed., pp. 513–524.

Bjelton, et al. *Availability of Cysteine and of L–2Oxo–Thiazolidine4–Carboxylic Acid as a Source of Cysteine in Intravenous Nutrition*, J. Parenter Enteral Nutr. Mar–Apr. 1990, vol. 14, No. 2, pp. 177–182. (Abstract).

Nappe, et al, *Electrophoretic Analysis of Alkylated Proteins of Human Hair from Various Ethnic Groups*, J. Soc. Cosmet. Chem., Mar./Apr. 1989, vol. 40, pp. 91–99.

Pruche, et al., *Changes in Glutathione Content in Human Hair Follicle Keratinocytes as a Function of Age of Donor: Relation with Glutathione Dependent Enzymes*, International Journal of Cosmetic Science, 1991, vol. 13, pp. 117–124.

Kermici, et al., *Evidence for an Age–Correlated Change in Glutathione Metabolism Enzyme Activities in Human Hair Follicle*, Mechanisms of Aging and Development, 1990, vol. 53, pp. 73–84.

Rao, et al., *Synthesis and Characterization of Defensin NP–1*, Int. J. Peptides Protein Res., 1992, vol. 40, pp. 507–514.

Angier, *From the Body Itself, Hope for a New Breed of Potent Antibiotics*, New York Times, Feb. 26, 1991, pp. 26–27.

Levy, et al., *Transport of Glutathione Diethyl Ester into Human Cells*, Proc. Natl. Acad. Sci., USA, Oct. 1993, vol. 90, pp. 9171–9175.

Jimenez, et al. *Treatment with ImuVert/N–Acetylcysteine Protects Rats from Cyclophosphamide/Cytarabine–Induced Alopecia*, Cancer Investigation, 1992, vol. 10, No. 4, pp. 271–276.

Astor et al, *Relationship, Between Intracellular GSH Levels and Hypoxic Cell Radiosensitivity*, Pharmac. Ther., vol. 39, pp. 115–121 (1988).

Chung et al, *L–2–Oxothiazolidine–4–Carboxylate as a Cysteine Precursor: Efficacy for Growth and Hepatic Glutathione Synthesis in Chicks and Rats*, American Institute of Nutrition, pp. 158–165 (1989).

*Guarding Against Cellular Glutathione Deficiency*, Nutritional Reviews, vol. 48, No. 9, pp. 346–348 (1990).

Martensson et al, *Glutathione Metabolism in the Lung: Inhibition of its Synthesis Leads to Lamellar Body an Mitochondrial Defects*, Proc. Natl. Acad. Sci. USA, vol. 86, pp. 5296–5300 (1989).

Martensson et al, *Mitochondrial Damage in Muscle Occurs After Marked Depletion of Glutathione and is Prevented by Giving Glutathione Monoester*, Proc. Natl. Acad. Sci. USA, vol. 86, pp. 471–475 (1989).

Meister, *Glutathione Esters Increase Cellular Glutathione Levels and are Thus Protective Against Oxidants and Other Compounds*, Abstract, (undated).

Roberts et al, *Prodrugs of L–Cysteine as Protective Agents Against Acetaminophen–Induced Hepatotoxicity. 2–(Polyhydroxyalkyl)– and 2–(Polyacetoxvalkyl)Thiazolidine–4(R)–Carboxylic Acids*, J. Med. Chem., 30, pp. 1891–1896 (1987).

Suthanthiran et al, *Glutathione Regulates Activation–Dependent DNA Synthesis in Highly Purified Normal Human T Lymphocytes Stimulated Via the CD2 and CD3 Antigens*, Proc. Natl. Acad. Sci. USA, vol. 87, pp. 3343–3347 (1990).

Roderer et al, *Cytokine–Stimulated Human Immunodeficiency Virus Replication is Inhibited by N–Acetvl–L–Cysteine*, Proc. Natl. Acad. Sci. USA, vol. 87, pp. 4884–4888 (1990).

Wellner et al, *Radioprotection by Glutathione Ester: Transport of Glutathione Ester into Human Lymphoid Cells and Fibroblasts*, Proc. Natl. Acad. Sci. USA, vol. 81, pp. 4732–4735 (1984).

Bounous et al. "Immunoenhancing Property of Dietary Whey Protein in Mice: Role of Glutathione", Clin. Invest. Med., vol. 12, No. 3, pp. 154–161.

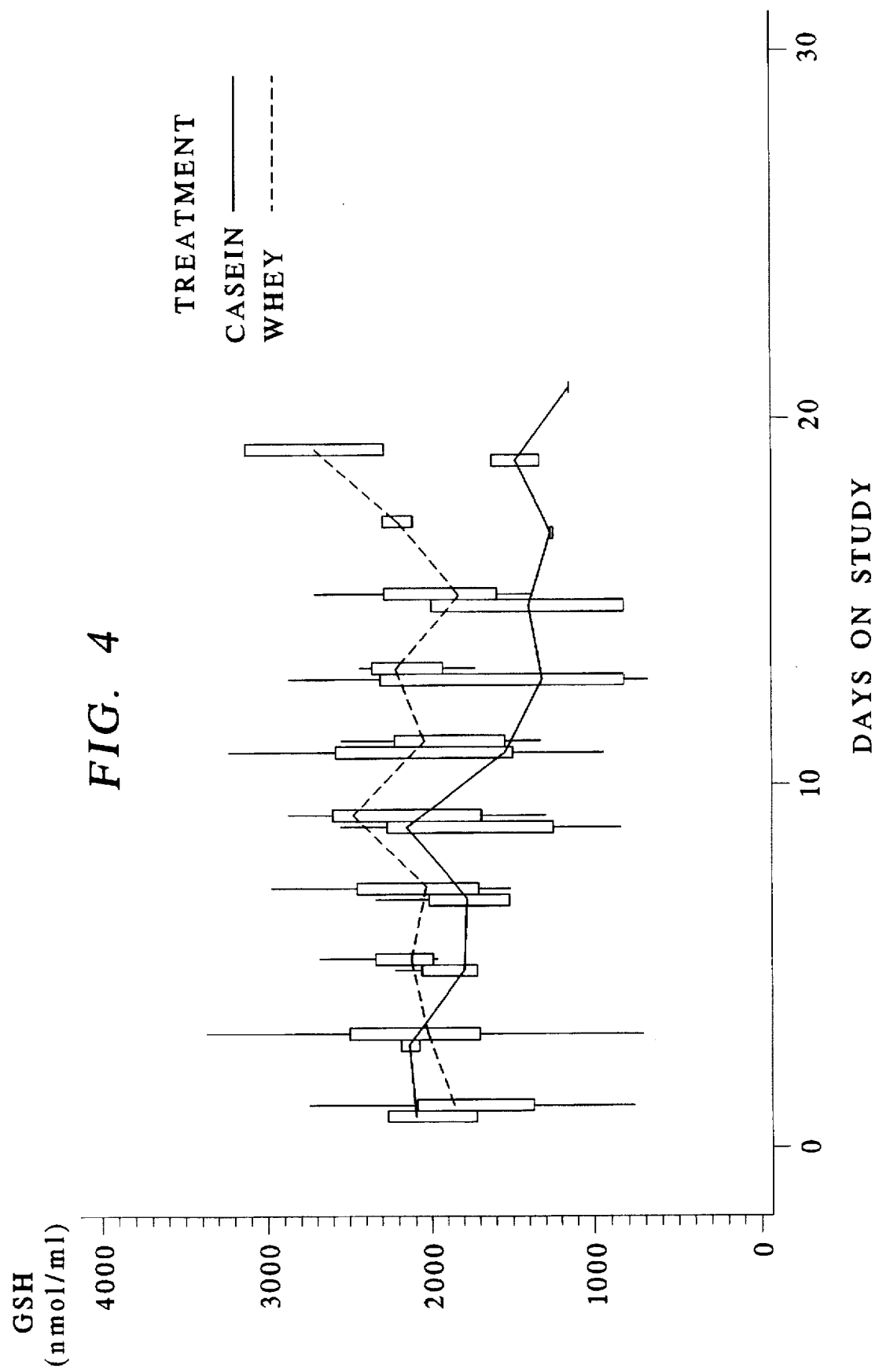

METHOD FOR INSURING ADEQUATE INTRACELLULAR GLUTATHIONE IN TISSUE

This is a continuation of application Ser. No. 08/659,111, filed Jun. 3, 1996, now abandoned which is a continuation of application Ser. No. 08/306,133, filed Sep. 14, 1994, now abandoned which is a continuation-in-part of application Ser. No. 07/650,222, filed Feb. 4, 1991 now abandoned.

BACKGROUND OF THE INVENTION

The present invention relates to insuring adequate levels of intracellular glutathione.

It has been suggested that by increasing intracellular glutathione levels certain benefits can be realized. Glutathione protects cells against free radicals, reactive oxygen intermediates, and toxic compounds that are both of endogenous and of exogenous origin. Meister, "New Aspects of Glutathione Biochemistry and Transport-Selective Alteration of Glutathione Metabolism", Nutrition Review, 42:397–410.

The intracellular biosynthesis of glutathione is rate limited by cysteine. However, increasing cysteine per se is limited because of its instability, and the use of oxidized cystine is limited due to its low solubility.

It has been proposed to infuse into a patient a precursor that will stimulate the intracellular synthesis of glutathione. To this end, N-acetylcysteine, a precursor of cysteine that is involved in the intracellular synthesis of glutathione has been infused, parenterally, in patients to raise the glutathione level. It is also known to infuse, parenterally, L-2-oxothiazolidine-4-carboxylate and glutathione esters to also stimulate intracellular glutathione production. See, U.S. Pat. Nos. 4,335,210; 4,434,158; 4,438,124; 4,647,571; 4,665,082; and 4,784,685.

Although the parenteral infusion of cysteine precursors as well as glutathione esters is believed to be an effective way to increase or maintain a sufficient level of intracellular glutathione, it would of course be desirable if the intracellular glutathione level could be maintained or increased through an enteral diet. This is especially true in view of the fact that a number of chronic disease states exhibit reduced or below normal cellular glutathione levels. One of the difficulties in increasing through an enteral regimen intracellular glutathione levels is that it is not typically possible merely to provide an enteral amino acid solution rich in cysteine. Cysteine typically will crystallize out as cystine in solution, e.g., an amino acid solution. Cystine is not readily biologically available to cells. Therefore, cysteine is not biologically available as a pharmaceutical.

Chung, et al., L-2-oxothiazolidine-4-carboxylate As A Cysteine Precursor: Efficacy for Growth and Hepatic Glutathione Synthesis in Chicks and Rats, American Institute of Nutrition (1990), sets forth experiments, by which they conclude, that orally administered L-2-oxothiazolidine-4-carboxylate is active as a cysteine precursor. In the experiments, they also administered, enterally, L-cysteine-HCl-H$_2$O. The paper also noted that "[i]t is well established that Cys [cysteine] is toxic when it is provided in excess. Rats given Cys via intraperitoneal injection show signs of toxicity, whereas those given OTC (on an equimolar basis to Cys) do not."

European published patent application 0 374 390 discusses a whey protein composition comprising a suitable concentrate that contains proteins in an essentially undenatured state. The application states that:

"It was shown, in controlled experiments, for the first time, that whey protein feeding of mice specifically enhances the immune response to sheep red blood cells (SRBC) and their resistance to pneumococcal infection, inhibits the development of DMH-induced colon cancer and increases tissue glutathione (GSH) levels independently of its nutritional quality.

The present invention shows the correlation between the undenatured conformation of whey protein concentrate (w.p.c.) and host immunoenhancement whereby chemical indices of denaturation are given and the demonstration that the same crucial role of molecular conformation (undenatured state) applies to GSH promotion, which is the other major biological activity of w.p.c.

Equally important is the demonstration that another protein source such as egg white, with the same high cysteine content as w.p.c. does not enhance GSH synthesis, further demonstrating the specificity of w.p.c. with respect to the described biological activity.

The GSH promoting activity of undenatured w.p.c. is sustained over time (3–4 months).

Whey and whey protein have been utilized from time immemorial for nutritional purposes. In addition, whey was recommended in folk and ancient medicine for the treatment of various diseases[1,2] and, in one instance, lifetime feeding of hamsters with a whey protein diet has been shown to promote longevity with no explanation given[3,4].

All these conditions appear to be somehow related to changes in glutathione which is a ubiquitous element exerting a protective effect against superoxide radicals and other toxic agents." (See page 2, lines 17–34.)

The European application also states that the biological activity of the whey protein "is actually dependent on the undenatured conformation of the proteins" (see page 13, lines 21–23). Additionally, the European application states that "the administration of glutathione itself is of little consequence on tissue glutathione levels, because it apparently cannot be transported intact across the cell membrane" (see page 6, lines 23–24).

The ability to give a composition orally that increases intracellular glutathione is highly desirable. However, all patient populations in need of same may not exhibit the same characteristics especially with respect to the bioavailability of the product to the patient. For patients having reduced or compromised gut function undenatured whey may not be absorbed in sufficient quantities so as to be readily bioavailable. Such patients with reduced gut function can include patients who suffer from: acquired immune deficiency syndrome (AIDS); Crohn's disease; chronic inflammatory bowel disease; short bowel syndrome; and inflammatory bowel reaction to radiation therapy. Not only do such patients typically have a reduced gut function, but, they may have reduced intracellular glutathione levels that should be elevated.

SUMMARY OF THE INVENTION

The present invention provides a method for insuring adequate intracellular glutathione levels in tissue. Pursuant to the present invention, a method for increasing intracellular glutathione levels in patients is provided comprising the steps of administering enterally to a patient having a compromised immune system a therapeutically effective amount of a solution including denatured proteins enriched in cysteine.

In an embodiment of the invention, the solution includes hydrolyzed whey.

In an embodiment of the invention, the solution includes hydrolyzed egg white protein.

In an embodiment, the present invention includes a method for increasing intracellular glutathione levels in a patient comprising enterally administering to the patient a therapeutically effective amount of a solution including denatured whey or egg white protein.

In an embodiment, a method for increasing glutathione levels in a patient is provided comprising the steps of administering enterally to the patient a sufficient amount of a denatured protein that includes at least 2.1% of its caloric content as cysteine.

In an embodiment, a method for enhancing immune function in a patient is provided comprising administering enterally to the patient a solution having at least 0.37% of its caloric content as cysteine.

An advantage of the present invention is that it provides a method for increasing glutathione levels in a patient.

A further advantage of the present invention is that it provides a method for enhancing immune function of a patient.

Additionally, an advantage of the present invention is that it provides a method for enhancing immune function of a patient who has a compromised immune function due to a disease state or trauma.

Furthermore, an advantage of the present invention is that it provides a method for increasing glutathione levels that can increase glutathione levels to a greater extent than the administration of an intact protein.

Still further, an advantage of the present invention is that it provides a method of treating stress in a patient.

Furthermore, an advantage of the present invention is that it provides a method for treating intensive care patients.

Additional features and advantages of the present invention are described in, and will be apparent from, the detailed description of the presently preferred embodiments.

BRIEF DESCRIPTION OF THE DRAWINGS

FIG. 4 illustrates graphically glutathione blood levels versus days for patients receiving a casein or denatured whey product pursuant to Example No. 1.

DETAILED DESCRIPTION OF THE PRESENTLY PREFERRED EMBODIMENTS

Figure 1A:
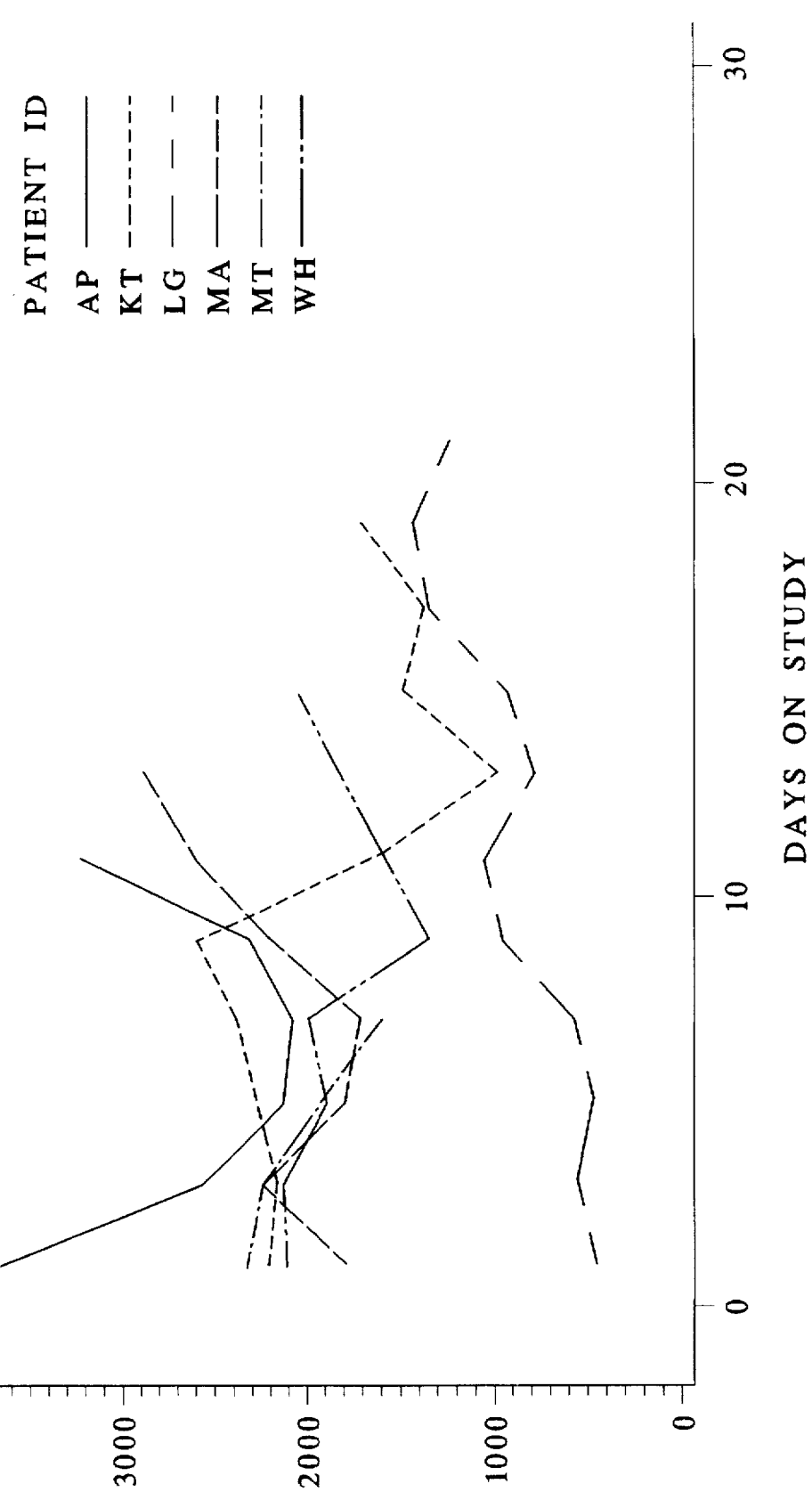
FIG. 1A illustrates graphically glutathione blood levels versus days for patients receiving a casein based formula pursuant to Example No. 1.

The present invention provides a method for insuring adequate intracellular glutathione levels in tissue.

Additionally, the present invention provides a method for increasing intracellular glutathione levels in a patient in need of same. The present invention can be used to treat stress patients, such as intensive care patients, patients having a compromised immune system, and/or patients having compromised gut function, for example.

The method comprises, in an embodiment, enterally administering a therapeutically effective amount of a solution including completely denatured and at least partially hydrolyzed proteins enriched in cysteine. Because the proteins are denatured and at least partially hydrolyzed, they are readily absorbed, even in a patient having compromised gut function.

In another embodiment, the method comprises administering to a patient a therapeutically effective amount of a solution including denatured protein and an amount of glutathione.

The inventors have found, that by administering a hydrolyzed protein including a sufficient amount of cysteine, that it is possible not only to maintain sufficient levels of glutathione in patients in need of increased glutathione levels, indeed, it is possible to increase the intracellular glutathione levels in those patients who have a depressed level of glutathione.

An advantage of present invention is that for a patient who requires increased levels of glutathione, it is possible to administer enterally the composition of the present invention and provide a sufficient level of intracellular glutathione. In fact, it is possible to increase the intracellular glutathione level to normal levels.

Typically, for example, an immune-compromised or intensive care unit patient has below normal cellular levels of glutathione. It is believed that a patient who has decreased glutathione levels is more susceptible to many disease states. It is therefore important to insure that cellular glutathione levels are maintained at near normal levels, or increased to meet those levels.

A number of such patients having reduced glutathione levels also have impaired or compromised gut functions. Examples of such patients include those suffering from: acquired immune deficiency syndrome (AIDS); Crohn's disease; chronic inflammatory bowel disease; short bowel syndrome; and inflammatory bowel reaction to radiation therapy. Due to the compromised gut function providing an intact protein, such as casein, would not provide a sufficiently bioavailable source of glutathione to the patient. By providing, in an embodiment, hydrolyzed protein enriched in cysteine, it is possible to insure adequate glutathione levels in such patients.

Intensive care patients typically are under physical stress from an event that led to their admission. Some of such stress is associated with oxidative damage. Glutathione plays a major role in protecting the body from oxidative damage. Additionally, cysteine which is rate limiting for glutathione synthesis, in vivo, may be conditionally essential in intensive care patients.

Especially with respect to intensive care patients, such patients may require special solutions to be fed, such as enteral solutions. Accordingly, the protein in such enteral products may be the sole source of a patient's cysteine. Although protein may be available from a variety of sources, casein and whey, the inventors have found that they provide to the patient significantly different levels of glutathione and cysteine in vivo; this is demonstrated by Example No. 1 set forth below.

Pursuant to the present invention, the metabolically stressed patient is fed a formulation that includes denatured, and at least partially hydrolyzed, protein. The protein includes at least 2.1% by caloric content cysteine. By way of example, hydrolyzed whey provides 2.3% of its calories as cysteine. Because the protein is denatured and includes cysteine at such a level, the glutathione levels and cysteine levels in the patient receiving same will be increased sufficiently to restore physiological glutathione levels and enhance immune function.

| Peptide Size: (number of amino acid residues) | Approximate molecular weight | Percentage by number |
|---|---|---|
| 1 (free amino acid) | 133 | 12% |
| 2–4 | 100–500 | 17% |
| 5–9 | 500–1000 | 38% |
| 10–40 | 1000–4600 | 28% |
| >40 | >4600 | 5% |

Average peptide size: 8 amino acid residues. The nutrient composition of PEPTAMEN® Liquid Elemental Diet is as follows:

NUTRIENT INFORMATION Serving Sie One can (500 ml)

| | | PER 500 ml | | PER 2000 ml | |
|---|---|---|---|---|---|
| | | AMOUNT | % U.S. RDA | AMOUNT | % U.S.RDA |
| NUTRIENT COMPOSITION | | | | | |
| CALORIES | kcal | 500 | ** | 2000 | ** |
| PROTEIN | g | 20.0 | 44 | 80 | 178 |
| CARBOHYDRATE | g | 63.5 | ** | 254 | ** |
| FAT** | g | 19.5 | ** | 78 | ** |
| Vitamin Composition | | | | | |
| VITAMIN A | IU | 1875 | 37 | 7500 | 150 |
| VITAMIN D | IU | 100 | 25 | 400 | 100 |
| VITAMIN E | IU | 10 | 33 | 40 | 133 |
| VITAMIN K | mcg | 62.5 | ** | 250 | ** |
| VITAMIN C | mg | 50 | 83 | 200 | 333 |
| THIAMINE (B$_1$) | mg | 0.75 | 50 | 3 | 200 |
| RIBOFLAVIN (B$_2$) | mg | 0.85 | 50 | 3.4 | 200 |
| NIACIN | mg | 10 | 50 | 40 | 200 |
| VITAMIN B$_6$ | mg | 1.5 | 75 | 6 | 300 |
| FOLIC ACID | mcg | 200 | 50 | 800 | 200 |
| PANTOTHENIC ACID | mg | 5 | 50 | 20 | 200 |
| VITAMIN B$_{12}$ | mcg | 3 | 50 | 12 | 200 |
| BIOTIN | mcg | 150 | 50 | 600 | 200 |
| CHOLINE | mg | 225 | ** | 900 | ** |

Pursuant to the present invention, preferably, denatured whey protein is administered to the patient. However, other products can be administered, such as hydrolyzed egg white protein.

A metabolically stressed patient should be provided with a minimum intake of cysteine of at least 0.3 grams (300 milligrams). This will maintain physiological levels of glutathione. However, if the patient's glutathione levels are depleted, pursuant to the present invention, the patient should be administered at least 1.2 grams (1,200 milligrams) of cysteine daily to restore depleted glutathione levels to normal physiological levels. For a patient having depleted glutathione levels, this requires providing a formulation that includes at least 0.37% of its calories as cysteine.

In an embodiment of the present invention, whey protein hydrolysate is administered to a patient. An example of an enteral diet that can be administered to the patient is PEPTAMEN®, Clintec Nutrition Company, Deerfield, Ill. PEPTAMEN® includes whey protein hydrolysate that provides 0.37% of the total calories of the product as cysteine. The peptide distribution of PEPTAMEN® is as follows:

Additionally, glutathione can be administered with the hydrolyzed protein to further assist in increasing intracellular glutathione levels. The glutathione can be added to the hydrolyzed protein that is enriched in cysteine.

In an embodiment, approximately 1 to about 2.8 grams of glutathione is added per milliliter of PEPTAMEN®.

By way of example, but not limitation, an experiment demonstrating the present invention will now be given.

EXAMPLE NO. 1

Study Design

This study was an open label, unblinded pilot study of the effects on whole blood glutathione and cysteine concentration of enteral feeding of critically ill patients. The study compared two enteral feeding formulas that differed only in the source of the protein component of the enteral feeding formula.

Study Population

Inclusion Criteria:
1. Greater than 18 years of age,
2. Expected to require at least eight days of enteral nutrition support,
3. Informed consent obtained from the patient or family.

Exclusion Criteria:
1. Less than 18 years of age,

2. Unable to obtain informed consent,

3. Not expected to require enteral nutrition support for at least eight days.

Patients enrolled in the study have the following general characteristics:

1. Closed head injury with GCS score of 4–8, and/or

2. Multiple trauma with multiple rib fractures and pulmonary contusions requiring mechanical ventilation, and/or 3. Twenty to fifty percent 2nd and 3rd degree burns, and/or 4. Multiple fractures requiring ventilatory support, and 5. Expected to require enteral nutrition support for a minimum of eight days.

Experimental Procedures

Nutrition Support.

The calculated goal rate for enteral nutrition support was 1.5 gm protein/kg/day and 30–35 non protein kcal/kg/day. These goal rates are those currently employed for critically ill patients. Patients were advanced to the goal feeding rate as the feeding was tolerated according to routine clinical guidelines such as abdominal distention and gastric or esophageal reflux. Patients for evaluation had to have received a minimum of eight days of enteral nutrition support. Daily intakes and clinical signs of intolerance to the enteral feeding were recorded.

Glutathione and Cysteine Measurements.

Three (3) ml blood samples were drawn prior to initiation of enteral feeding and every two days during the duration of enteral feeding support. Whole blood samples were prepared by a standard procedure developed by the Metabolic Assessment Laboratory at the University of Florida, Gainsville. Assays for whole blood glutathione and cysteine were performed using a HPLC procedure at the Metabolic Assessment Laboratory. Glutathione concentration as determined in whole blood was corrected for the patient's hematocrit and cysteine concentrations was corrected for the patient's "plasmacrit" (1-Hct).

Results

Baseline Analysis.

Patient Characteristics.

The patient characteristics at study entry thought to be of significance to glutathione status of critical care patients are presented below.

|  | MEAN | (range) | YES | NO |
|---|---|---|---|---|
| Age | 48 | (28–70) | | |
| Injury severity score | 23.8 | (7–41) | | |
| Days between injury and study entry | 19.5 | (5–49) | | |
| Organ dysfunction at study entry | | | 0 | 11 |
| On mechanical ventilation | | | 8 | 3 |
| Septic at study entry | | | 9 | 2 |
| Nutrition prior study entry | | | 11 | 0 |
| Nutritionally deprived for greater than 3 days | | | 7 | 4 |
| Glutathione and cysteine concentrations. | | | | |

Based on previous studies (unpublished) normal hematocrit corrected blood glutathione values are approximately 2300±300 micromoles/ml. As can be seen from Table 1 (below), eight of the fourteen patients analyzed in this study had glutathione concentrations within or above this range.

Two patients (Patients 8 and 12) had greatly reduced glutathione concentrations in the range of those reported in severely stressed ARDS patients.

Based on the same prior studies, the normal "plasmacrit" corrected blood cysteine concentrations are approximately 210±40 micromoles/ml. As seen in Table 1, six of the fourteen patients analyzed in this study had cysteine concentrations that were below this normal range. There was no clear correspondence between patients with low glutathione values and patients with low cysteine concentrations.

TABLE 1

| | | day 1 | GSH day 3 | day 5 | day 7 | day 9 | day 11 |
|---|---|---|---|---|---|---|---|
| 1 | whey | 2000.0 | 2060.2 | 2044.5 | 1659.1 | 1555.1 | 2179.5 |
| 1" | whey | 1653.3 | 2036.5 | 2415.1 | 2928.3 | 2400 | |
| 2 | whey | 2037.7 | 3306.9 | 2000.0 | 2689.8 | 2540.1 | 2062.5 |
| 3 | whey | 2202.2 | 2368.8 | 2142.9 | 2222.9 | 2845.9 | 2530.6 |
| 4 | whey | 1240.3 | 1770.0 | 2281.3 | 2180.9 | 2619.6 | 1743.8 |
| 5 | whey | 1794.4 | 1715.3 | 2123.6 | 1930.1 | 1912.4 | 1395.3 |
| 12 | whey | 859.0 | 817.3 | 1381.5 | 1568.6 | 1356.0 | 1448.8 |
| 18 | whey | 2729.8 | 2639.7 | 2659.8 | 1839.3 | 2573.0 | 1596.8 |
| | | 14516.7 | 16714.8 | 17048.3 | 17018.9 | 17802.5 | 13743.8 |
| Mean | whey | 1814.6 | 2089.3 | 2131.0 | 2127.4 | 2225.3 | 1963.4 |
| | | 100.0 | 115.1 | 117.4 | 117.2 | 122.6 | 108.2 |
| 7 | casein | 1759.4 | 2186.7 | 1757.9 | 1677.8 | 2166.7 | 2568.2 |
| 8 | casein | 435.5 | 532.4 | 460.4 | 557.4 | 933.6 | 1026.7 |
| 10 | casein | 3611.9 | 2531.6 | 2080.8 | 2041.3 | 2273.6 | 3184.1 |
| 14 | casein | 2163.9 | 2126.2 | 226.6 | 2341.1 | 2547.4 | 1587.8 |
| 16 | casein | 2068.2 | 2090.6 | 1850.0 | 1948.6 | 1313.0 | 1541.1 |
| 20 | casein | 2274 | 2199 | 1824 | 1566 | | |
| | | 12313 | 11669 | 10202 | 10132 | 9234 | 9908 |
| Mean | casein | 2052 | 1945 | 1700 | 1689 | 1847 | 1982 |
| | | 100.0 | 94.8 | 82.9 | 90.0 | 96.6 | 77.3 |

| | | day 13 | day 15 | day 17 | day 19 | day 21 |
|---|---|---|---|---|---|---|
| 1 | whey | | | | | |
| 1" | whey | | | | | |
| 2 | whey | 2294.3 | 1894.3 | 2128.6 | 3080.0 | |
| 3 | whey | 2429.9 | 2689.0 | 2290.6 | 2288.8 | |
| 4 | whey | 1762.3 | 1827.7 | | | |
| 5 | whey | | | | | |
| 12 | whey | 2154.2 | 1448.8 | | | |
| 18 | whey | | | | | |
| | | 8640.6 | 7859.7 | 4419.2 | 5368.8 | |
| Mean | whey | 2160.2 | 1964.9 | 2209.6 | 2684.4 | |
| | | 119.0 | 108.3 | 121.8 | 147.9 | |
| 7 | casein | 2835.6 | | | | |
| 8 | casein | 766.7 | 910.0 | 1316.7 | 1393.3 | 1216.7 |
| 10 | casein | | | | | |
| 14 | casein | 955.1 | 1454.8 | 1327.8 | 1660.5 | |
| 16 | casein | 1787.3 | 2025.4 | | | |
| 20 | casein | | | | | |
| | | 6345 | 4390 | 2644 | 3054 | 1217 |
| Mean | casein | 1586 | 1463 | 1322 | 1527 | 1217 |
| | | 77.3 | 71.3 | 64.4 | 74.4 | 59.3 |

Protein and Cysteine Intake.

At the protein intakes recorded in this study, the daily intake of cysteine was in the range of 1.45 to 1.85 grams per day in the patients receiving the hydrolyzed whey protein based diet (PEPTAMEN® elemental diet). Patients on the casein based diet (Nutren) received in the range of 0.13 to 0.23 grams of cysteine per day.

Summary of Analyses

Figure 1B:
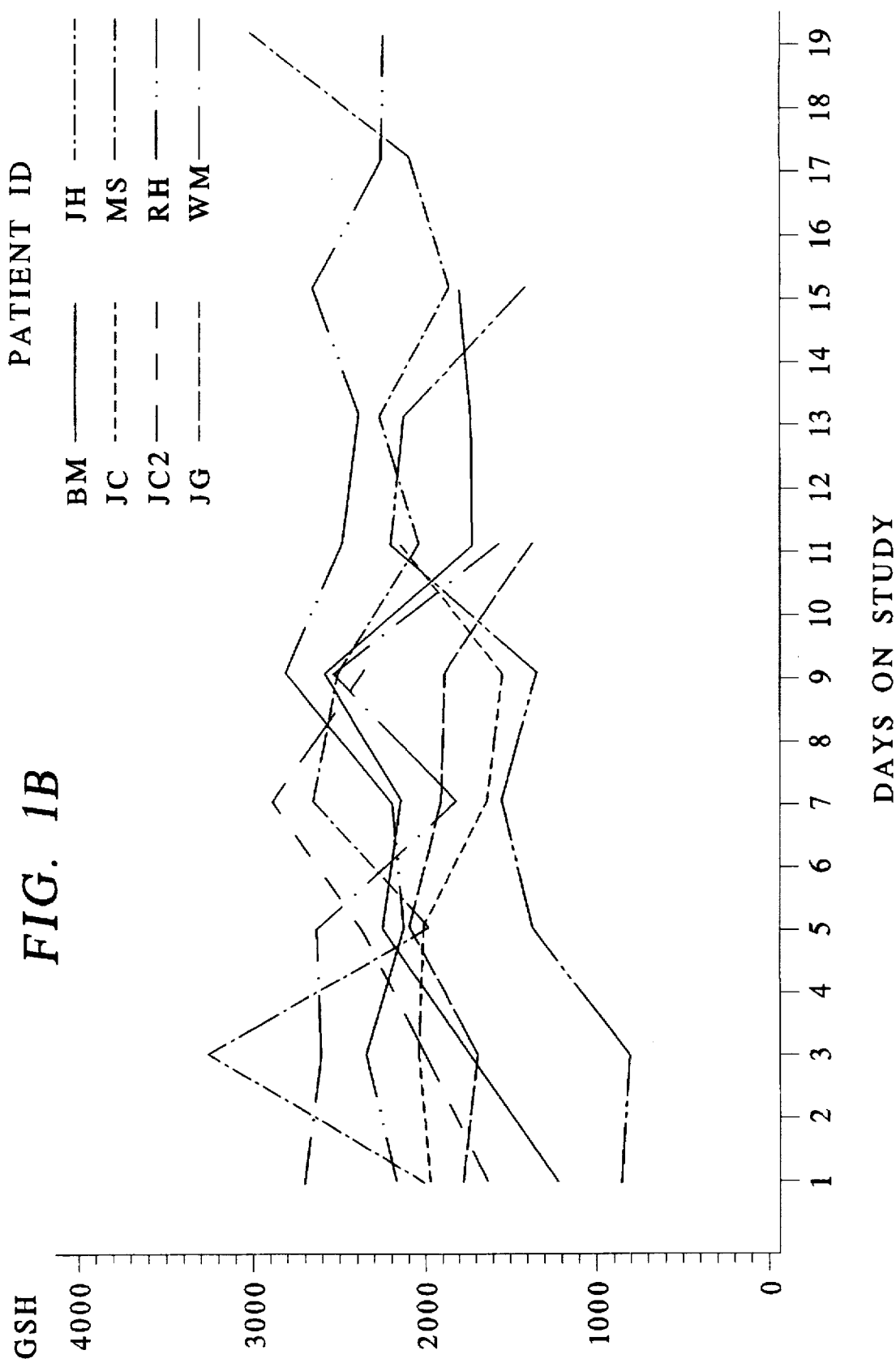
FIG. 1B illustrates graphically glutathione blood levels versus days for patients receiving a denatured whey based formula pursuant to Example No. 1.
Figure 2A:
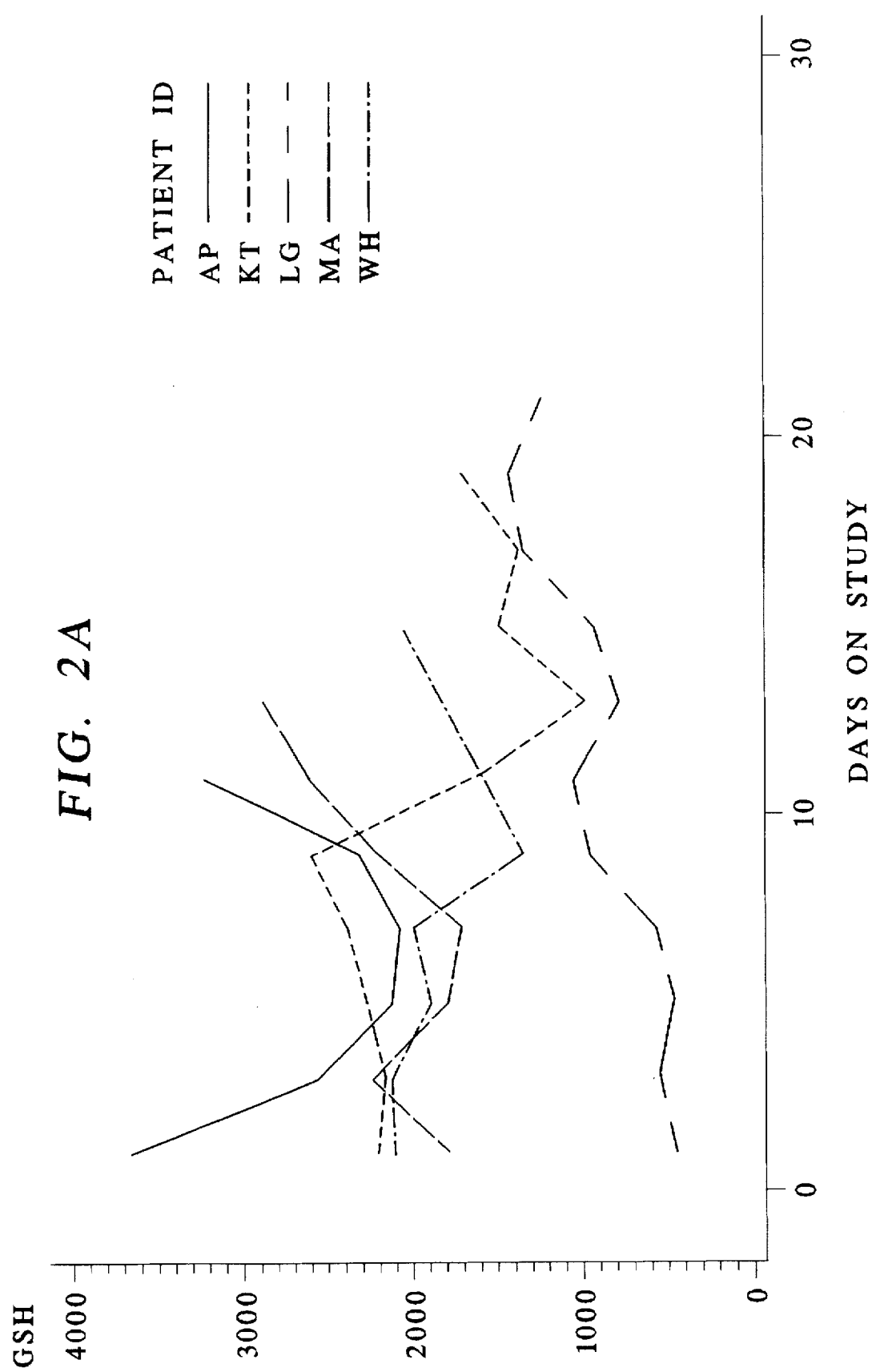
FIG. 2A illustrates graphically glutathione blood levels versus days for patients receiving a casein based formula pursuant to Example No. 1.
Figure 2B:
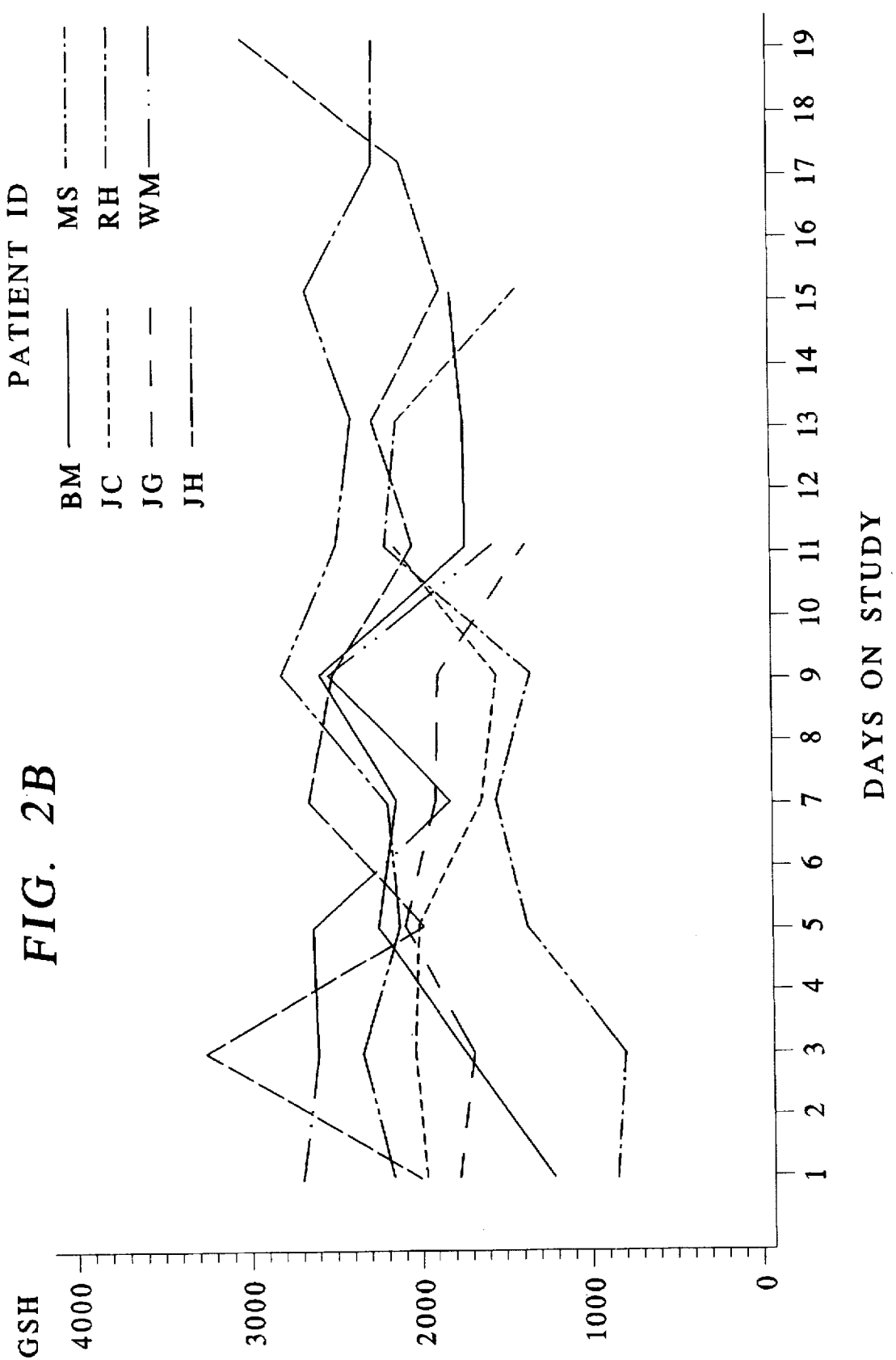
FIG. 2B illustrates graphically glutathione blood levels versus days for patients receiving a denatured whey based formula pursuant to Example No. 1.

Analysis of variance with repeated measures was used to analyze the data. The independent variables in the analysis were treatment (whey-vs. casein based diets), days on study, and the treatment by day interaction. Three analyses were performed; these analyses are illustrated graphically in FIGS. 1–3 specifically the figures illustrate the results graphically for: all patients in the study (FIGS. 1A and 1B); all patients who were in the study for at least 11 days (FIGS.

Figure 3A:
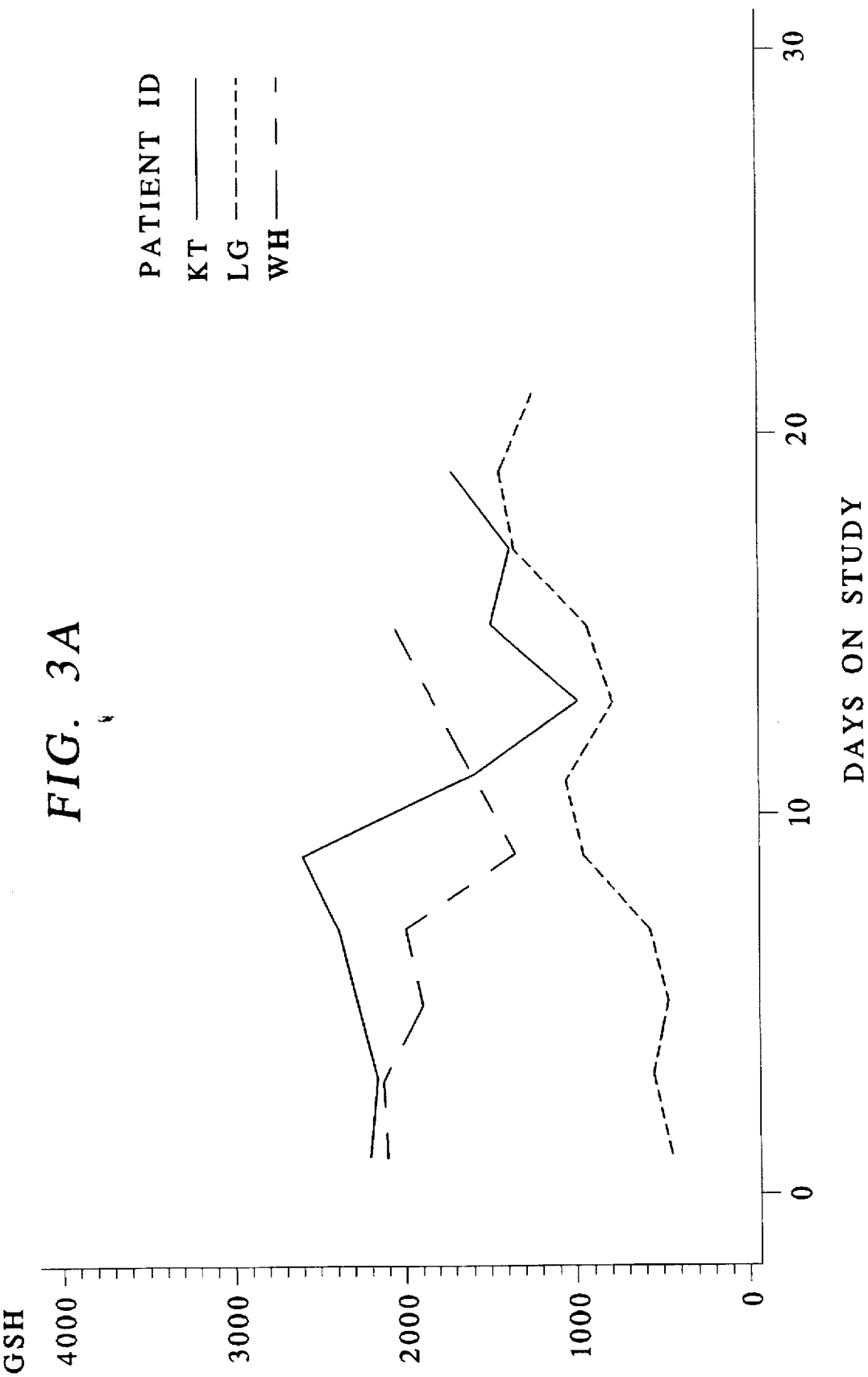
FIG. 3A illustrates graphically glutathione blood levels versus days for patients receiving a casein based formula pursuant to Example No. 1.
Figure 3B:
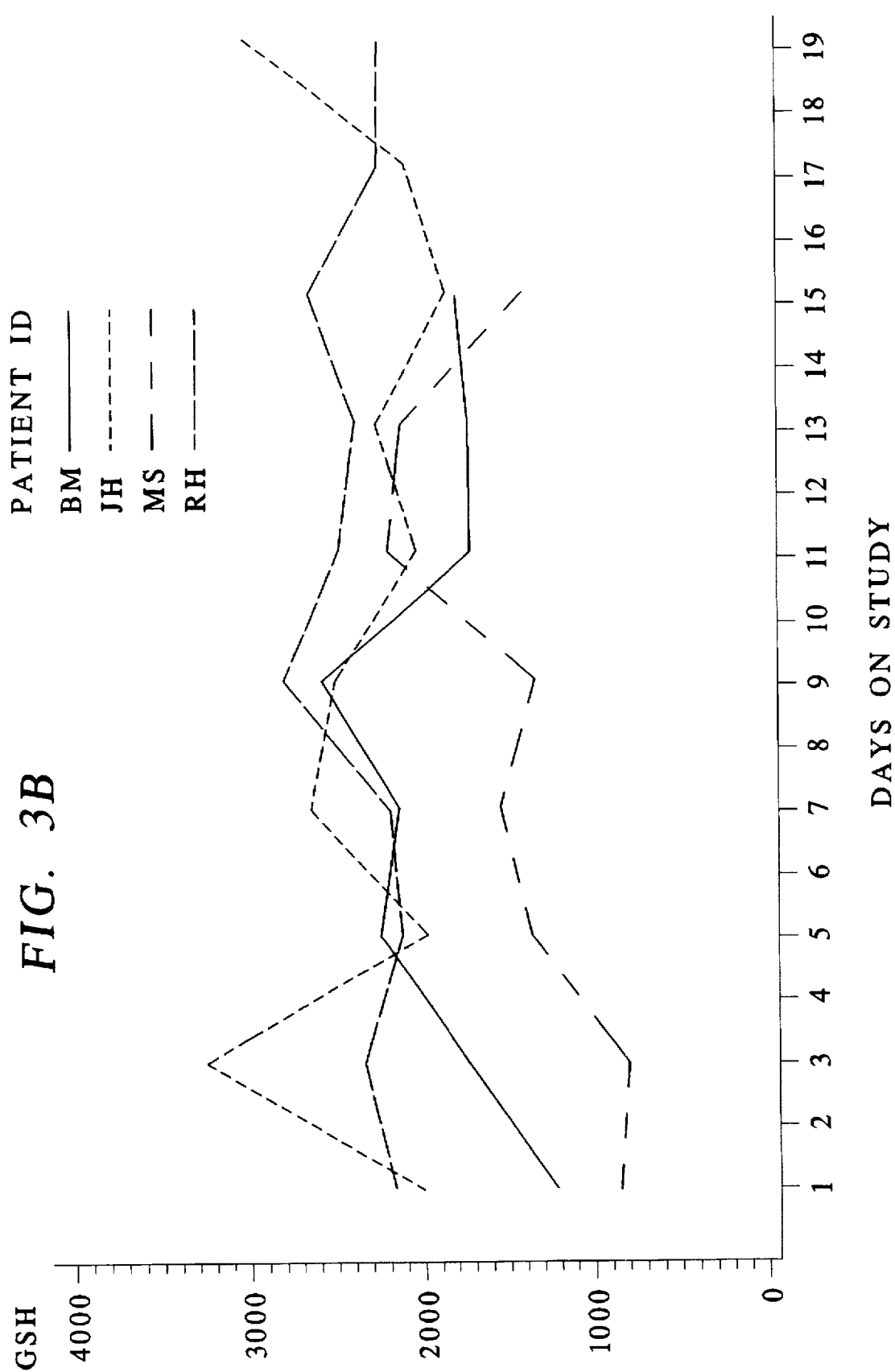
FIG. 3B illustrates graphically glutathione blood levels versus days for patients receiving a denatured whey based formula pursuant to Example No. 1.

2A and 2B); and all patients who were in the study for at least 15 days (FIGS. 3A and 3B). Table 2 summarizes the p-values from these analyses.

TABLE 2

Summary of p-values From Analysis of Variance with Repeated Measures

| Analysis | Treatment Group | Days in the study | Treatment by Day Interaction |
|---|---|---|---|
| All patients | 0.35 | 0.95 | 0.46 |
| At least 11 days | 0.43 | 0.94 | 0.78 |
| At least 15 days | 0.10 | 0.55 | 0.57 |

Table 3 (below) summarizes the whole blood GSH levels and Table 4 (below) summarizes the change from baseline of whole blood GSH for both groups. FIG. 4 graphically summarizes these same data comparing the results for a denatured and hydrolyzed whey diet versus an intact casein diet.

TABLE 3

Summary of Whole Blood GSH

| TRT | DAY | N | MEAN | STD | MIN | MAX |
|---|---|---|---|---|---|---|
| casein | 1 | 6 | 2052.00 | 1019.43 | 435 | 3612 |
|  | 3 | 6 | 1944.83 | 709.83 | 532 | 2532 |
|  | 5 | 6 | 1700.33 | 633.06 | 460 | 2229 |
|  | 7 | 6 | 1688.67 | 618.59 | 557 | 2341 |
|  | 9 | 5 | 1847.00 | 688.01 | 934 | 2547 |
|  | 11 | 5 | 1981.60 | 873.20 | 1027 | 3184 |
|  | 13 | 4 | 1586.25 | 943.72 | 767 | 2836 |
|  | 15 | 3 | 1463.33 | 557.55 | 910 | 2025 |
|  | 17 | 2 | 1322.50 | 7.78 | 1317 | 1328 |
|  | 19 | 2 | 1526.50 | 188.80 | 1393 | 1660 |
|  | 21 | 1 | 1217.00 |  | 1217 | 1217 |
| whey | 1 | 8 | 1814.50 | 578.45 | 859 | 2730 |
|  | 3 | 8 | 2089.25 | 729.85 | 817 | 3307 |
|  | 5 | 8 | 2131.13 | 372.30 | 1381 | 2660 |
|  | 7 | 8 | 2127.38 | 481.49 | 1569 | 2928 |
|  | 9 | 8 | 2225.25 | 547.02 | 1356 | 2846 |
|  | 11 | 7 | 1963.43 | 399.54 | 1395 | 2531 |
|  | 13 | 4 | 2160.00 | 288.27 | 1762 | 2430 |
|  | 15 | 4 | 1965.00 | 520.97 | 1449 | 2689 |
|  | 17 | 2 | 2210.00 | 114.55 | 2129 | 2291 |
|  | 19 | 2 | 2684.50 | 559.32 | 2289 | 3080 |

TABLE 4

Summary of GSH - Change From Baseline

| TRT | DAY | N | MEAN | STD | MIN | MAX |
|---|---|---|---|---|---|---|
| casein | 1 | 6 | 0.000 | 0.00 | 0 | 0 |
|  | 3 | 6 | −107.167 | 509.78 | −1080 | 430 |
|  | 5 | 6 | −351.667 | 609.40 | −1531 | 65 |
|  | 7 | 6 | −363.333 | 669.95 | −1571 | 177 |
|  | 9 | 5 | −160.600 | 835.68 | −1338 | 499 |
|  | 11 | 5 | −26.000 | 669.75 | −576 | 809 |
|  | 13 | 4 | −20.250 | 967.67 | −1209 | 1077 |
|  | 15 | 3 | −92.333 | 593.54 | −709 | 475 |
|  | 17 | 2 | 23.000 | 1214.81 | −836 | 882 |
|  | 19 | 2 | 227.000 | 1033.79 | −504 | 958 |
|  | 21 | 1 | 782.000 |  | 782 | 782 |
| whey | 1 | 8 | 0.000 | 0.00 | 0 | 0 |
|  | 3 | 8 | 274.750 | 460.07 | −90 | 1269 |
|  | 5 | 8 | 316.625 | 423.51 | −70 | 1041 |
|  | 7 | 8 | 312.875 | 715.77 | −891 | 1275 |
|  | 9 | 8 | 410.750 | 568.59 | −445 | 1380 |
|  | 11 | 7 | 125.857 | 776.78 | −1133 | 1376 |
|  | 13 | 4 | 575.250 | 497.79 | 228 | 1295 |
|  | 15 | 4 | 380.250 | 352.79 | −144 | 590 |
|  | 17 | 2 | 90.000 | 1.41 | 89 | 91 |
|  | 19 | 2 | 564.500 | 675.29 | 87 | 1042 |

Listing of Whole Blood GSH Data

| Treatment Group | Patient ID | Day | GSH | Day 11 | Day 15 |
|---|---|---|---|---|---|
| whey | BM4 | 1 | 1240 | * | * |
|  |  | 3 | 1770 | * | * |
|  |  | 5 | 2281 | * | * |
|  |  | 7 | 2181 | * | * |
|  |  | 9 | 2620 | * | * |
|  |  | 11 | 1744 | * | * |
|  |  | 13 | 1762 | * | * |
|  |  | 15 | 1828 | * | * |
| whey | JC1 | 1 | 2000 | * |  |
|  |  | 3 | 2060 | * |  |
|  |  | 5 | 2045 | * |  |
|  |  | 7 | 1659 | * |  |
|  |  | 9 | 1555 | * |  |
|  |  | 11 | 2179 | * |  |
| whey | JC21 | 1 | 1653 |  |  |
|  |  | 3 | 2036 |  |  |
|  |  | 5 | 2415 |  |  |
|  |  | 7 | 2928 |  |  |
|  |  | 9 | 2400 |  |  |
| whey | JG5 | 1 | 1794 | * |  |
|  |  | 3 | 1715 | * |  |
|  |  | 5 | 2124 | * |  |
|  |  | 7 | 1930 | * |  |
|  |  | 9 | 1912 | * |  |
|  |  | 11 | 1395 | * |  |
| whey | JH2 | 1 | 2038 | * | * |
|  |  | 3 | 3307 | * | * |
|  |  | 5 | 2000 | * | * |
|  |  | 7 | 2690 | * | * |
|  |  | 9 | 1540 | * | * |
|  |  | 11 | 2063 | * | * |
|  |  | 13 | 2294 | * | * |
|  |  | 15 | 1894 | * | * |
|  |  | 17 | 2129 | * | * |
|  |  | 19 | 3080 | * | * |
| whey | MS12 | 1 | 859 | * | * |
|  |  | 3 | 817 | * | * |
|  |  | 5 | 1381 | * | * |
|  |  | 7 | 1569 | * | * |
|  |  | 9 | 1356 | * | * |
|  |  | 11 | 2235 | * | * |
|  |  | 13 | 2154 | * | * |
|  |  | 15 | 1449 | * | * |

*This patient's data included in analysis.

List of Whole Blood GSH Data

| Treatment Group | Patient ID | Day | GSH | Day 11 | Day 15 |
|---|---|---|---|---|---|
| whey | RH3 | 1 | 2202 | * | * |
|  |  | 3 | 2369 | * | * |
|  |  | 5 | 2143 | * | * |
|  |  | 7 | 2223 | * | * |
|  |  | 9 | 2846 | * | * |
|  |  | 11 | 2531 | * | * |
|  |  | 13 | 2430 | * | * |
|  |  | 15 | 2689 | * | * |
|  |  | 17 | 2291 | * | * |

-continued

List of Whole Blood GSH Data

| Treatment Group | Patient ID | Day | GSH | Day 11 | Day 15 |
|---|---|---|---|---|---|
|  |  | 19 | 2289 | * | * |
| whey | WM18 | 1 | 2730 | * |  |
|  |  | 3 | 2640 | * |  |
|  |  | 5 | 2660 | * |  |
|  |  | 7 | 1839 | * |  |
|  |  | 9 | 2573 | * |  |
|  |  | 11 | 1597 | * |  |

*This patient's data included in analysis.

As illustrated graphically in FIG. 4, whole blood glutathione levels were increased and stayed increased using denatured and hydrolyzed whey protein as compared to intact protein (casein). Thus, the present invention provides a method for increasing glutathione levels, in vivo. As compared to the use of intact protein, the method of the present invention increases glutathione levels and maintains the increased levels.

By way of example, but not limitation, contemplative examples of the present invention will now be given.

Contemplative Example 1

A 32-year-old white male has been known to be HIV positive for seven years. He was essentially free of symptoms until two years ago when he had a complicated medical course following an upper respiratory tract infection. During the course of this illness he lost approximately 15% of his usual body weight. Following recovery from this illness, he was relatively free of symptoms except for occasional episodes of diarrhea of unknown etiology. Despite dietary and nutritional counseling he was unable to regain significant weight due, in part, to compromised gut function.

The use of a hydrolyzed whey protein dietary supplement was recommended to aid in increasing nutrient intake and to aid in absorption of nutrients. He was able to drink approximately one liter of this supplement increasing his calorie intake by approximately 1000 kcal per day and to increase his protein intake by 40 grams per day.

He gained six pounds in the first two weeks of dietary supplementation and continued to gain two to three pounds between biweekly clinic visits despite somewhat reduced intake of the supplement. He remained symptom-free and has had no further episodes of diarrhea.

Plasma glutathione and cysteine levels were found to be at the levels seen in normal healthy individuals at 4 weeks following initiation of supplementation.

Contemplative Example 2

A 54-year-old white male has known to be HIV positive for five years. In the last six months he has had several opportunistic infectious episodes including two lung infections that required hospitalization. During the second hospitalization he was placed on total parenteral nutrition (TPN) for eight days to increase nutrient intake and restore a significant weight loss (18% of usual body weight). Before discharge from the hospital he was transitioned to oral intake using an enteral feeding formula based on hydrolyzed whey protein. He continued to use the preparation as an occasional dietary supplement after release from the hospital.

During the period when he received TPN, a plasma amino acid profile was performed. Among several deviations from the normal amino acid profile was a 90% reduction in plasma cysteine concentration. This observation was followed by an analysis of plasma glutathione and white blood cell glutathione concentrations. Both plasma and white blood cell glutathione concentrations were less than 10% of normal values.

These analyses were repeated one week after hospital discharge following two weeks of oral intake of the enteral supplement. At this time both plasma cysteine and glutathione were at the low end of normal values. White blood cell glutathione levels were at approximately 60% of normal values.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for increasing intracellular glutathione levels in a stressed patient comprising the steps of enterally administering to the patient a therapeutically effective amount of a denatured and at least partially hydrolyzed protein that includes at least 2.1% cysteine by caloric content.

2. The method of claim 1 wherein the protein includes whey.

3. The method of claim 1 wherein the protein includes egg white protein.

4. The method of claim 1 wherein the patient initially has a less than physiological normal level of glutathione.

5. The method of claim 1 wherein the patient is an intensive care patient.

6. The method of claim 1 wherein at least 1.2 grams of cysteine are administered to the patient daily.

7. The method of claim 1 wherein the patient has a compromised immune system.

8. A method for enhancing the immune system of a metabolically stressed patient comprising the steps of enterally administering to the patient a composition that includes at least 0.37% of its caloric content as cysteine.

9. The method of claim 8 wherein the protein includes whey.

10. The method of claim 8 wherein the protein includes egg white protein.

11. The method of claim 8 wherein the patient initially has a less than physiological normal level of glutathione.

12. The method of claim 8 wherein the patient is an intensive care patient.

13. The method of claim 8 wherein at least 1.2 grams of cysteine are administered to the patient daily.

14. A method for increasing intracellular glutathione levels in a metabolically stressed patient having reduced intracellular levels of glutathione comprising administering to the patient an enteral composition that includes a sufficient amount of a denatured and at least partially hydrolyzed whey protein to increase the intracellular glutathione level of the patient.

15. The method of claim 14 wherein the composition includes glutathione.

16. The method of claim 14 wherein at least 1.2 grams of cysteine are administered to the patient daily.

17. The method of claim 14 wherein the composition provides at least 0.37% of its caloric content as cysteine.

18. A method for increasing intracellular glutathione levels in a patient having a compromised immune system and reduced intracellular levels of glutathione comprising administering to the patient an enteral composition that includes at least 0.37% of its caloric content as cysteine and includes a denatured and partially hydrolyzed protein in an amount sufficient to increase the intracellular glutathione level of the patient.

19. The method of claim 18 wherein the composition includes glutathione.

20. The method of claim 18 wherein at least 1.2 grams of cysteine are administered to the patient daily.

* * * * *